United States Patent [19]
Wilder et al.

[11] 3,942,526
[45] Mar. 9, 1976

[54] ALARM SYSTEM FOR INTRAVENOUS INFUSION PROCEDURE

[76] Inventors: Joseph R. Wilder, 151 W. 86th St., New York, N.Y. 10024; Maurice S. Kanbar, 34 W. 13th St., New York, N.Y. 10011; Cynthia K. Wilder, 151 W. 86th St., New York, N.Y. 10024

[22] Filed: Mar. 3, 1972

[21] Appl. No.: 231,601

[52] U.S. Cl.... 128/214 E; 128/214 C; 128/DIG. 13; 137/399; 137/412; 200/84 C; 222/67; 340/244 A; 116/110
[51] Int. Cl.² .......................................... A61M 5/14
[58] Field of Search ........ 128/214 R, 214 C, 214 E, 128/214 Z, 227, DIG. 13; 200/84 C; 340/239 R, 244 A; 137/399, 432, 412; 222/17, 67; 116/110; 119/14.14, 78

[56] References Cited
UNITED STATES PATENTS

| | | | |
|---|---|---|---|
| 2,681,654 | 6/1954 | Ryan et al. | 128/214 C |
| 2,914,631 | 11/1959 | Reburn | 200/84 C |
| 3,105,511 | 10/1963 | Murphy | 128/214 C X |
| 3,114,478 | 12/1963 | Hilkemeier et al. | 222/17 |
| 3,216,419 | 11/1965 | Scislowicz | 128/214 C |
| 3,389,603 | 6/1968 | Jacobs | 340/244 AX |
| 3,478,184 | 11/1969 | Cofoid | 200/84 C |
| 3,543,752 | 12/1970 | Hesse et al. | 128/214 E |
| 3,667,464 | 6/1972 | Alligood | 128/214 C |

*Primary Examiner*—Dalton L. Truluck

[57] ABSTRACT

An alarm system operative in conjunction with a venocylsis set which includes a drop chamber coupled to the output of a fluid bottle. The alarm system is provided with a float disposed in the drop chamber and responsive to the level of fluid pool therein. A proximity switch sensitive to the float position is removably attached to the exterior of the drop chamber to produce a switching action when the fluid level falls below a predetermined value. An alarm circuit is coupled to the proximity switch to generate a warning signal when the switching action occurs.

6 Claims, 5 Drawing Figures

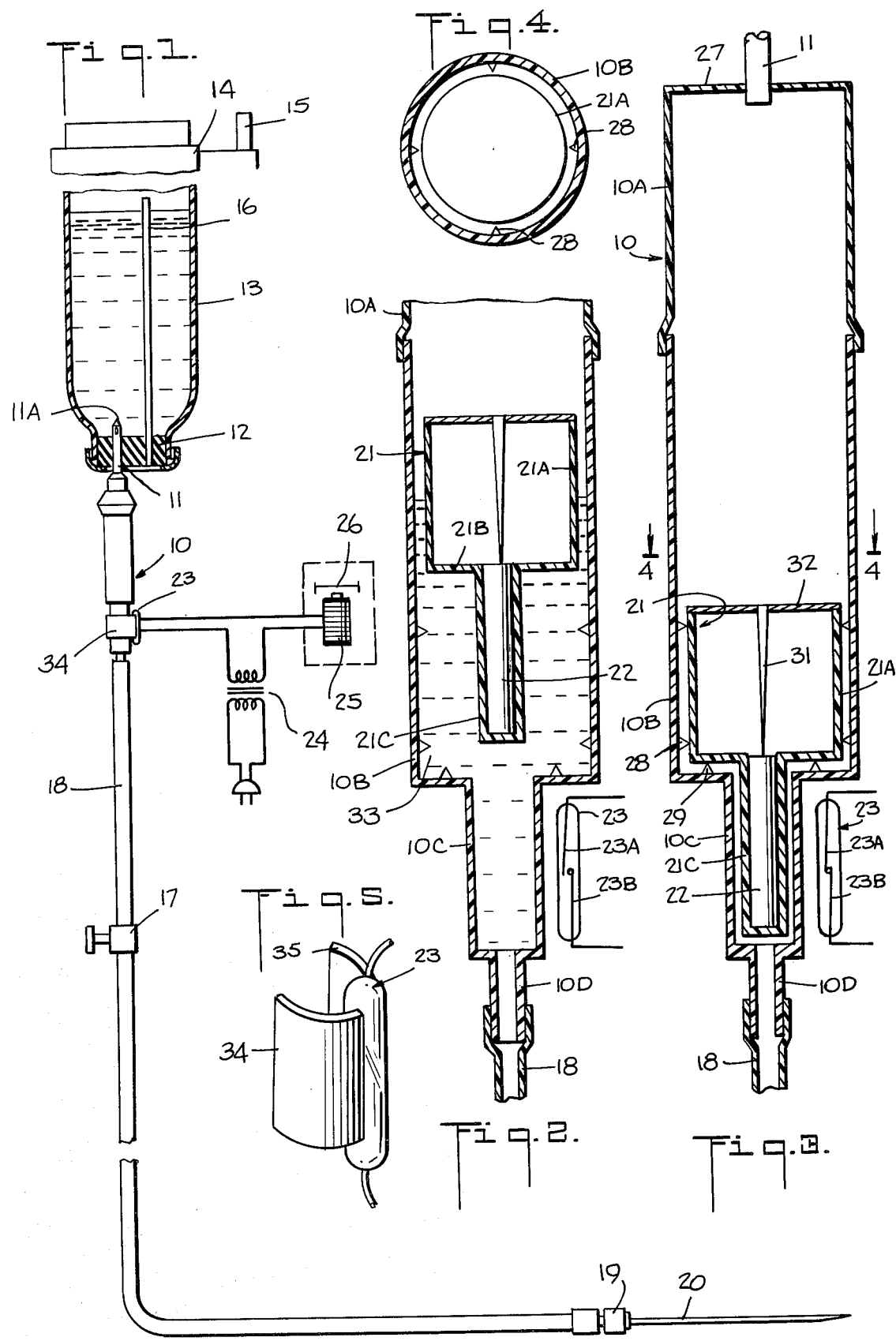

ALARM SYSTEM FOR INTRAVENOUS INFUSION PROCEDURE

BACKGROUND OF THE INVENTION

This invention relates generally to intravenous infusion procedures wherein fluid is gravity-fed from a fluid container to a patient, and in particular to an alarm system for indicating when the container is exhausted.

The intravenous infusion of fluids by gravity flow is now a common procedure in modern hospitals. Among the fluids administered are plasma, blood, glucose and saline solutions. Intravenous injection over a protracted period is usually carried out by reducing fluid flow from the elevated container to a succession of discrete drops. This is effected by means of a drop chamber coupled to the output of the container through a drip tube. In practice, a delivery pipe is extended from the drop chamber to a lower position where the fluid is to be injected into the patient through a hollow needle or catheter.

It is often of vital importance that the fluid bottle or container be replaced with a fresh supply when the container is drained. This requires regular attendance or frequent inspection by a nurse or hospital orderly. Should an emergency arise or other factors come into play distracting the attention of the nurse or orderly, the container may become empty and remain unchanged. In some instances, failure to continue the supply of fluid may be fatal or harmful to the patient. Because the fluids being administered frequently contain life-giving drugs such as insulin, anti-biotics, vitamins, hormones or electrolytes, the failure to continue intravenous therapy, regardless of its cause, may have catastrophic consequences. With existing shortages of qualified hospital personnel, such failures are not uncommon.

Various types of monitoring or alarm systems have heretofore been devised to signal when the fluid being received by a patient from a container has drained to a low level. A typical alarm system for this purpose makes use of a spring by which the fluid container is suspended from an elevated support. As the fluid discharges and the weight of the container diminishes, the amount of spring extension is reduced to a point at which an electrical switch mounted at a preset position, is caused to close, thereby activating an alarm signal serving to alert the nurse to take whatever action is then appropriate.

The characteristics of the weighing spring and the related arrangement of parts must be preselected in accordance with the weight of the container load. Thus, the spring arrangement for a 500 ml. bottle of blood is necessarily different from that dictated by a 250 ml. bottle. A spring weighing arrangement is therefore not a universal monitor for any type of container, but is limited to a specific fluid load. Moreover, it is cumbersome and unreliable.

Other known forms of monitoring or warning devices for use in conjunction with intravenous flow arrangements, include electrical networks, oscillators, amplifiers and other elaborate circuits connected to the output of capacitative, electro-optical and other sophisticated forms of sensors. For example, in one such device which is attachable to the exterior of the fluid container to indicate when it is nearly empty, a capacitance bridge is provided, two of whose capacitances have dielectrics defined by the fluid in this container. When fluid falls to a given level, the resultant bridge output activates a nurse's call system or alarm.

Apart from the complexity and high cost of known types of electrical alarm systems, there is the further problem of safety, for intravenous infusion is sometimes conducted within an oxygen tent in which electrical sparking cannot be tolerated. Prior systems fail to provide adequate protection against sparking or high voltage shorts that may lead to sparking and fatal explosions.

SUMMARY OF THE INVENTION

In view of the foregoing, the chief object of this invention is to provide an alarm system which obviates the drawbacks incident to systems heretofore used in conjunction with intravenous infusion procedures, the present system being simple, efficient and reliable.

More specifically, it is an object of this invention to provide a low-cost alarm system including a drop chamber which encloses a float having a permanent magnet sealed therein, the float level reflecting the fluid condition of the container coupled to the chamber and being sensed by a magnetically-responsive proximity switch.

Among the significant advantages of the invention are the following:

A. The magnetic float incorporated in the special drop chamber is the only addition that need be made to existing forms of disposable venocylsis sets for fluid administration; hence the cost of a set including the float is not significantly greater than the cost of the set without the float. Since such disposable sets are used by hospitals in large quantities, this cost factor is an important practical consideration for both hospital and patients.

B. The proximity switch, which is detachably coupled to the drop chamber to sense the float position, may be quickly and easily attached and detached, so that no particular skill or special training is necessary to teach nurses and attendants how to operate the alarm system.

C. The flat which encloses the magnet is in the form of a sterile shell which may be made of the same plastic material as the venocylsis set and in no way contaminates the sterile fluid flowing through the drop chamber.

D. The proximity switch may be in the form of a reed switch actuated in the presence of the float magnet, which switch may be hermetically sealed to isolate the switch and any sparks produced therein from the ambient atmosphere.

E. The alarm associated with the switch may be in the form of a simple solenoid that is energized by alternating current when the proximity switch is closed, to produce an alternating magnetic field sustaining a diaphragn in vibration, thereby producing a distinctive signal tone without, however, creating any sparking.

Briefly stated, these objects are attained in an alarm system operating in conjunction with a venocylsis set including a drop chamber coupled to the output of a raised fluid container. The alarm system is constituted by a float disposed within the drop chamber and responsive to the level of fluid therein, a proximity switch being detachably coupled to the exterior of the chamber and being responsive to the float position to produce a switch closure only when the fluid level falls below a predetermined value. An alarm circuit is coupled to the switch to produce a warning signal when the switch closes.

In a preferred embodiment of the invention, the drop chamber is defined by a collapsible cylindrical upper section which is manually depressible to produce a suction force for initiating the flow of fluid from the associated container, and a more rigid cylindrical lower section having a tubular well projecting below the floor thereof, the end of the well communicating with a flexible pipe terminating in a suitable coupling for an injection needle or catheter.

Concentrically disposed within the lower section of the drop chamber is a float defined by an enclosed cylindrical shell having a tubular nose projecting axially from the base thereof, the nose being received concentrically within the well. Held within the nose is a permanent magnet element. Removably attached to the well of the drop chamber is the proximity switch which preferably is of the magnetically responsive reed type that is actuated by the magnet element only when the nose of the float lies fully within the well.

In operation, drops of fluid from the container form a pool in the lower section of the drop chamber, causing the float to rise to a level that depends on the depth of the pool, thereby raising the nose and the magnet element therein. When however, the container fluid is depleted, the pool is emptied and the magnet element descends into the well to actuate the switch and sound the alarm.

OUTLINE OF THE DRAWINGS

For a better understanding of the invention as well as other objects and further features thereof, reference is made to the following detailed description to be read in conjunction with the accompanying drawings, wherein:

FIG. 1 shows an intravenous infusion assembly operating in conjunction with an alarm system according to the invention;

FIG. 2 shows the drop chamber of the assembly in the condition that exists when the supply of fluid in the container is adequate;

FIG. 3 illustrates the drop chamber in its condition when the fluid supply is depleted;

FIG. 4 is a transverse section taken through the drop chamber in the plane indicated by line 4—4 in FIG. 3; and FIG. 5 is a perspective view of the reed switch associated with the drop chamber.

DESCRIPTION OF THE INVENTION

Referring now to the drawings and more particularly to FIG. 1, the alarm system in accordance with the invention is adapted to operate in conjunction with an intravenous infusion set or assembly which may be of any commercially available type, save for a special drop chamber, generally designated by numeral 10.

Drop chamber 10 is provided with a drip tube 11, the upper end 11A of which is needle-pointed in order to pierce the penetrable stopper 12 of a bottle 13 containing a fluid such as glucose, to be administered to a patient. Bottle 13 is inverted and is supported at an elevated position with respect to the patient by means of a clamp 14 serving to attach the bottle to a stand 15. An air-intake tube 16 anchored in the stopper provides a conduit between the air space above the fluid level in the bottle and the atmosphere, thereby avoiding bubbling.

The drop rate is adjusted by means of screw-type clamp 17 or equivalent valve means attached to a flexible pipe 18 leading from drop chamber 10 to a suitable coupler 19 connectable to a hollow needle 20 or catheter for injecting the fluid. The degree to which pipe 18 is restricted by the clamp determines the flow rate.

To sense whether the bottle fluid is depleted, the drop chamber is provided with a float, generally designated by numeral 21, within which a permanent-magnet element 22 is hermetically sealed. The position of the float within the drop chamber is detected by a magnetically responsive proximity switch 23 which is normally open but is caused to close only when the magnet position reflects a depleted fluid supply.

The closure of the switch completes a circuit between the secondary of a voltage step-down transformer 24 coupled to the A-C power line and a solenoid 25. When the solenoid is energized, it produces an alternating electro-magnetic field which sustains a diaphragm 26 in vibration to produce a distinctive alarm tone, calling attention to the depletion of the fluid in the bottle and the need for appropriate action.

The advantage of this type of alarm, as against a conventional buzzer, is that no make-and-break contacts are involved, as with the interrupter on a buzzer. Such contacts give rise to sparking that may be hazardous in certain hospital environments.

The invention is by no means limited to this particular type of A-C alarm, and in practice, the alarm may be of the battery-operated type or tied in with a nurse's call system, or with a central annunciator or a flashing-light indicator. In practice, the alarm may be incorporated into a central hospital monitor.

Referring now to FIGS. 2, 3 and 4, drop chamber 10 is shown in greater detail. The chamber is constituted by a collapsible cylindrical upper section 10A and a rigid cylindrical lower chamber 10B bonded thereto. The upper end of the chamber is closed by a cap 27 through which the lower end of drip tube 11 extends.

Upper section 10A is formed of flexible plastic transparent material such as polyethylene or vinyl, so that this section may be manually compressed to create a suction force to initiate the flow of liquid from the container. The lower section, which is joined to the upper section, is formed by a relatively rigid plastic material whose dimensions are fixed. Projecting axially from the floor of the lower section and extending downwardly therefrom is a tubular well 10C terminating in a coupling sleeve 10D to which flexible pipe 18 is connected.

Floating within lower section 10B is the float 21. The float is constituted by a cylindrical shell 21A whose outer diameter is somewhat smaller than the inner diameter of the lower section, whereby the shell lies concentrically within the lower section and is slidable therein to define an annular passage therebetween allowing for the unimpeded flow of fluid.

This concentricity is maintained by four equispaced centering bosses 28 formed on the inner surface of the lower section, as shown in FIG. 4. Similar bosses 29 on the floor of the lower section maintain a flow space between this floor and the bottom 21B of the float shell.

Depending axially from the bottom 21B of the float shell 21A and extending downwardly therefrom, is a tubular nose 21C that is concentrically disposed within well 10C when the float rests on the bottom of the lower section. Placed within nose 21C is a rod-shaped permanent-magnet element 22. This element is held in place by a finger 31 projecting from the underside of cover 32 on the float.

Thus, in assembling the float, one first inserts the magnet in the nose, and then places the cover over the float, the cover being sealed to the rim of the shell. The float is made of plastic material and the magnet sealed therein is therefore isolated from the fluid passing through the drop chamber.

In operation, a fluid pool 33 is created in the lower section of the drop chamber by the succession of drops fed therein, the depth of the pool being such as to cause float 21 to rise to a point at which magnet 22 is largely withdrawn from well 10C, as shown in FIG. 2.

When, however, the fluid supply from the bottle is depleted and the pool in the chamber is drained, the float then rests on the bottom of the lower section and the magnet lies within well 10C. The magnet is then in close proximity to the magnetically responsive reed contacts 23A and 23B of the reed switch, causing these contacts to come together to effect switch closure.

The contacts are hermetically sealed within a protective glass or plastic envelope; hence sparks between contacts are isolated from the environment. The reed switch, which is a permanent part of the installation, is removably attached to well 10C of the drop chamber by means of resilient wings 34 and 35, adapted to embrace the well.

Thus the disposable infusion assembly may be discarded after a single use, and when the alarm system is to be employed with a new assembly, one has merely to clip the reed switch onto the well of the drop chamber of the new assembly.

It will be evident from the foregoing that the only change necessary to convert any existing form of disposable intravenous infusion set is the substitution of a drop chamber having a magnetic-element float therein in accordance with the invention, the set otherwise being unmodified. With a float chamber of this type, one has merely to clip on the reed switch to afford a warning signal when the bottle is empty of fluid. Thus, no significant change in procedure is involved, and any nurse or orderly capable of installing existing forms of infusion sets, can make use of the invention.

While there have been shown and described preferred embodiments of an alarm system for intravenous infusion procedures, it will be appreciated that many changes and modifications may be made therein without, however, departing from the essential spirit of the invention.

In practice, the upper section of the drop chamber need not be collapsible, for other means may be used to initiate the flow of fluid from the fluid container. The chamber need not be a drop chamber, for other means may be used to obtain a controlled flow from the fluid container. Also, instead of bottles of glass or other rigid material, a collapsible fluid container may be used, in which event one may dispense with an air vent.

We claim:

1. An intravenous infusion arrangement comprising a container; a drop chamber, provided with a drip tube, fluid from said container being conducted by gravity flow into said drop chamber to produce a fluid pool therein and from the chamber through a pipe leading to a hollow needle; and an alarm system to provide a warning signal when the fluid supply from the container approaches exhaustion, said system including:

a. a float disposed in said chamber which is caused to assume a position therein depending on the depth of said pool, the float having transverse dimensions which are smaller than those of the chamber interior to define a space therebetween which provides an uninterrupted flow passage to said pipe regardless of the position of the float, said chamber having a collapsible upper section and a rigid lower section, b. a permanent magnet sealed within said float, c. a magnetically-responsive proximity switch means attached to said chamber to produce a switching action only when the position of said float is indicative of the approach of fluid exhaustion, and d. an alarm circuit coupled to said switch means to produce a warning signal when said switching action occurs.

2. An alarm system as set forth in claim 1, wherein said lower section is provided with spacer bosses on the inner surface thereof to engage the wall of the float to maintain said annular passage.

3. An alarm system as set forth in claim 1, wherein said lower section is provided with a tubular well projecting downwardly therefrom, and said float is provided with a nose receivable within said well, said magnet being placed in said nose.

4. An alarm system as set forth in claim 3, wherein said float is provided with a cap having a finger which extends toward said nose to engage the end of said magnet to hold it in place.

5. An alarm system as set forth in claim 3, wherein said proximity switch means is a sealed reed switch.

6. An alarm system as set forth in claim 5, wherein said reed switch is provided with resilient wings adapted to clamp said switch onto said well.

* * * * *